United States Patent [19]
Baldwin et al.

[11] Patent Number: 5,175,284
[45] Date of Patent: Dec. 29, 1992

[54] TRICYCLIC THIENOTHIOPYRANS AS PHARMACEUTICAL INTERMEDIATES

[75] Inventors: John J. Baldwin, Gwynedd Valley; Gerald S. Ponticello, Lansdale; Kenneth L. Shepard, North Wales; Theresa M. Williams, Harleysville, all of Pa.

[73] Assignee: Merck & Co., Inc., Rahway, N.J.

[21] Appl. No.: 777,814

[22] Filed: Oct. 15, 1991

[51] Int. Cl.⁵ .............................. C07D 495/18
[52] U.S. Cl. .................... 540/581; 546/80; 548/431; 548/430
[58] Field of Search .......... 540/581; 546/80; 548/431, 430

[56] References Cited

U.S. PATENT DOCUMENTS

| | | | |
|---|---|---|---|
| 4,174,396 | 11/1979 | Jarque et al. | 546/80 |
| 4,619,939 | 10/1986 | Maren | 514/363 |
| 4,677,115 | 6/1987 | Baldwin et al. | 514/432 |
| 4,797,413 | 1/1989 | Baldwin et al. | 514/432 |
| 5,011,942 | 4/1991 | Blacklock et al. | 549/23 |

FOREIGN PATENT DOCUMENTS 0022396  2/1979  Japan .

Primary Examiner—Joseph Paul Brust
Assistant Examiner—Mary Susan H. Gabilan
Attorney, Agent, or Firm—William H. Nicholson; Joseph F. DiPrima

[57] ABSTRACT

Intermediates are described for preparing conformationally constrained tricyclic thienothiopyran compounds that are topically effective carbonic anhydrase inhibitors useful in the treatment of ocular hypertension and glaucoma associated therewith.

3 Claims, No Drawings

TRICYCLIC THIENOTHIOPYRANS AS PHARMACEUTICAL INTERMEDIATES

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. Many of these agents, however, also have other characteristics, e.g. membrane stabilizing activity, that are not acceptable for chronic ocular use. (S)-1-tert-Butylamino[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired opthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Benzothiophene-2-sulfonamides, benzenesulfonylthiophene-2-sulfonamides, and thieno[2,3-b]thiopyran-2-sulfonamides are also reported to be carbonic anhydrase inhibitors topically effective in reducing intraocular pressure in U.S. Pat. Nos. 4,668,697; 4,585,787; and 4,797,413, respectively.

U.S. Pat. No. 4,619,939 discloses a process and composition for reducing intraocular pressure and reducing aqueous humor formation by applying topically to the cornea an effective amount of an aqueous solution of a carbonic anhydrase inhibitor having the following properties:

a. sufficiently soluble in water to form at least a 3 mM solution at pH 8.2 or a pKa of not greater than 7.3;

b. ether partition coefficient of at least 1.0;

c. chloroform partition coefficient of at least 0.01;

d. dissociation constant against carbonic anhydrase of not more than $3 \times 10^{-8}$ molar;

e. first order rate constant for penetration of the sulfonamide through a living rabbit cornea of at least 0.005 $hr^{-1}$;

f. not injurious to the cornea; and g. stable in aqueous solution and in contact with the cornea.

OBJECTS OF THE INVENTION

It is an object of the present invention to provide pharmaceutical intermediates for preparing the compounds of the present invention that are effective in treating ocular hypertension and glaucoma associated therewith. This and other objects of the present invention will be apparent from the following description.

SUMMARY OF THE INVENTION

This invention relates to the preparation of pharmaceutical intermediates for preparing conformationally constrained tricyclic thienothiopyrans of the structural formula

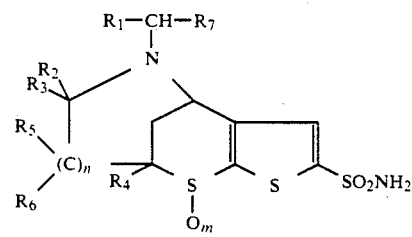

wherein $R_1$ is H, unsubstituted or substituted lower alkyl, lower alkenyl, aryl or aralkyl wherein the aryl groups optionally are substituted by lower alkyl, halogen, $CF_3$, OH, lower alkyl-$S(O)_m$, or lower alkoxy; $R_2$, $R_3$, $R_5$, $R_6$ and $R_7$ are independently H or alkyl or $R_2$ and $R_3$ together are $=O$; $R_4$ is H, lower alkyl, lower alkenyl or lower alkyl substituted by lower alkenyloxy, hydroxy, alkoxy, hydroxyalkoxy, alkoxyalkoxy, hydroxyalkoxyalkoxy, alkylamino, hydroxyalkylamino, alkoxyalkylamino, hydroxyalkoxyalkylamino, alkyl-$S(O)_m$-, hydroxyalkyl-$S(O)_m$-, alkoxyalkyl-$S(O)_m$-, hydroxyalkoxyalkyl-$S(O)_m$-, alkyl-$S(O)_m$-alkoxy, hydroxyalkyl-$S(O)_m$-alkoxy, alkyl-$S(O)_m$alkyl-$S(O)_m$ and hydroxyalkyl-$S(O)_m$alkyl-$S(O)_m$; and m and n are independently 0, 1, or 2.

DETAILED DESCRIPTION OF THE INVENTION

The pharmaceutical intermediates of the present invention are useful to prepare compounds having the structural formula

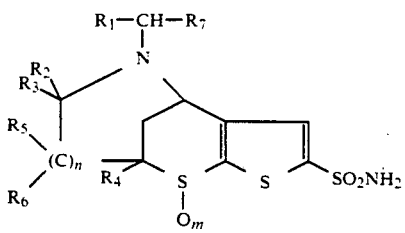

having a cis configuration, the enantiomers and mixtures thereof or an opthalmologically acceptable salt thereof wherein:

$R_1$ is
1) H;
2) lower alkyl, preferably $C_{1-6}$ alkyl, lower alkenyl, preferably $C_{1-6}$alkenyl, or lower alkyl, preferably $C_{1-6}$ alkyl, substituted with F, OH, $C_{1-5}$alkyl-$S(O)_m$ or $C_{1-5}$alkoxy;
3) aryl or aralkyl wherein the aryl groups optionally are substituted by $C_{1-3}$alkyl, halogen, $CF_3$, OH or $C_{1-3}$alkoxy;

$R_2$, $R_3$, $R_5$, $R_6$, and $R_7$ and $R_8$ are independently H or lower alkyl, preferably $C_{1-4}$ alkyl, or $R_2$ and $R_3$, or $R_7$ and $R_8$ together are =O; and $R_4$ is
1) H, lower alkyl, preferably $C_{1-6}$;
2) $C_{1-6}$alkyl substituted with
   a) hydroxy,
   b) $C_{1-3}$alkyl-O—,
   c) hydroxy$C_{1-3}$alkyl-O—,
   d) $C_{1-3}$alkyl-O—$C_{1-3}$alkyl-O—,
   e) hydroxy$C_{1-3}$alkyl-O—$C_{1-3}$alkyl-O—,
   f) $C_{1-3}$alkylNH—,
   g) hydroxy$C_{1-3}$alkylNH—,
   h) $C_{1-3}$alkyl-O—$C_{1-3}$alkylNH—;
   i) hydroxy$C_{1-3}$alkyl-O—$C_{1-3}$alkylNH—;
   j) $C_{1-3}$alkyl-$S(O)_m$-,
   k) hydroxy$C_{1-3}$alkyl-$S(O)_m$-,
   l) $C_{1-3}$alkyl-O—$C_{1-3}$alkyl-$S(O)_m$-,
   m) hydroxy$C_{1-3}$alkyl-O—$C_{1-3}$alkyl-$S(O)_m$-,
   n) $C_{1-3}$alkyl-$S(O)_m$-$C_{1-3}$alkyl-O—
   p) $C_{1-3}$alkyl-$S(O)_m C_{1-3}$alkyl-$S(O)_m$-
   q) HO—$C_{1-3}$alkyl-$S(O)_m C_{1-3}$alkyl-$S(O)_m$-
   r) $C_{2-6}$ alkenyloxy;
3) $C_{2-6}$alkenyl and m and n are independently 0, 1 or 2.

Preferred compounds of the present invention are those wherein $R_1$, $R_2$, $R_3$, $R_5$ and $R_6$ are independently H or $C_{1-6}$alkyl, and $R_4$ is H, $C_{1-6}$alkyl or $C_{1-6}$alkyl substituted by hydroxy, alkoxy, hydroxyalkoxy, alkoxyalkoxy, alkylamino, alkoxyalkylamino, alkyl-$S(O)_m$-, hydroxy$C_{1-3}$alkyl-$S(O)_m$-, $C_{1-3}$alkyl-$S(O)_m$-$C_{1-3}$alkyl-$S(O)_m$-, $C_{1-3}$alkyl-O—$C_{1-3}$alkyl-$S(O)_m$-, $C_{1-3}$alkyl-$S(O)_m$-$C_{1-3}$alkyl-O—, or $C_{2-6}$alkenyl; and m and n are independently 0, 1 or 2.

Most preferred compounds are 4-ethyl-2-[2-(2-methoxyethoxy)ethyl]-2,3,4,5-tetrahydro-2,5-methanothieno[3,2-f]-1,4-thiazepine-7-sulfonamide-1,1-dioxide hydrochloride, 5-(4-methoxybenzyl)-2-methyl-3,4,5,6-tetrahydro-2H-2,6-methanothieno[3,2-g]-1,5-thiazocine-8-sulfonamide-1,1-dioxide, 5-(4-methoxybenzyl)-2-methoxypropyl-3,4,5,6-tetrahydro-2H-2,6-methanothieno[3,2-g]-1,5-thiazocine-8-sulfonamide-1,1-dioxide, 2-methyl-3,4,5,6-tetrahydro-2H-2,6-methanothieno[3,2-g]-1,5-thiazocine-8-sulfonamide-1,1-dioxide hydrochloride, 2-methoxypropyl-3,4,5,6-tetrahydro-2H-2,6-methanothieno[3,2-g]-1,5-thiazocine, 5-isobutyl-4-oxo-3,4,5,6-tetrahydro-2H-2,6-methanothieno[3,2-g]-1,5-thiazocine-8-suflonamide, 5-isobutyl-4-oxo-3,4,5,6-tetrahydro-2H-2,6-methanothieno[3,2-g]-1,5-thiazocine-8-sulfonamide-1,1-dioxide, 5-isobutyl-3,4,5,6-tetrahydro-2H-2,6-methanothieno-[3,2-g]-1,5-thiazocine-8-sulfonamide-1,1-dioxide hydrochloride, 5-propyl-3,4,5,6-tetrahydro-2H-2,6-methanothieno[3,2-g]-1,5-thiazocine-8-sulfonamide-1,1-dioxide hydrochloride, 2,5-methanothieno[3,2-f]-1,4-thiazepine-7-sulfonamide-4-propyl-2,3,4,5-tetrahydro-1,1-dioxide hydrochloride and cis(S,S)2,5-methanothieno[3,2-f]-1,4-thiazepine-7-sulfonamide-4-ethyl-2,3,4,5-tetrahydro-1,1-dioxide hydrochloride.

The compounds of the present invention can be prepared by treating a compound of formula 1 with lithium bis(trialkylsilyl)amide, preferably lithium bis(trimethylsilyl)amide, in a polar solvent such as, for example, tetrahydrofuran (THF) for from about 5 minutes to about one hour under an inert atmosphere, for example, nitrogen, at lowered temperature of from about −100° C. to about −50° C., followed by treatment with N,N-dialkylmethylammonium iodide, preferably N,N-dimethylmethylammonium iodide, while permitting the temperature to rise from about 5° C. to about 25° C. The compound of formula 2 is recovered and a

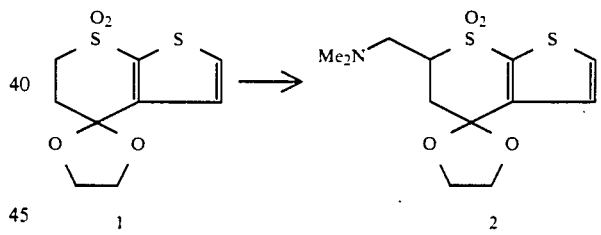

mixture of it and an alkyl iodide, preferably methyl iodide, is stirred at about ambient temperature for about 24 hours, dissolved in a polar solvent such as, for example, acetonitrile, and treated with 1,8-diazabicyclo-[5.4.0]undec-7-ene to give the product of formula 3.

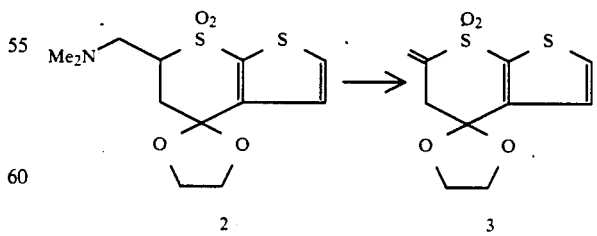

Sodium methanethiolate is added to a mixture of the compound of formula 3 and a polar solvent such as, for example, THF. After from about 5 minutes to about 2 hours, the solvent is removed, preferably in vacuo, to yield the compound of formula 4.

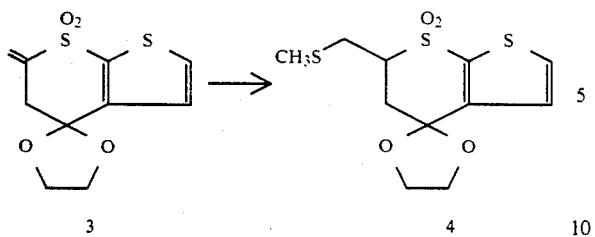

A solution of the compound of formula 4 in acid, preferably HCl, and a polar solvent, for example, THF, is heated to reflux for from about 10 minutes to about 2 hours after which the solvent is removed, preferably under reduced pressure, to yield the compound of formula 5.

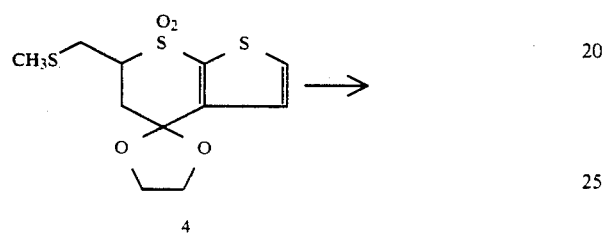

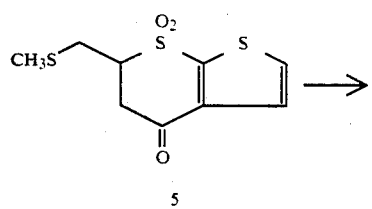

Sodium borohydride is added to a solution of the compound of formula 5 in a polar solvent, for example, ethanol, methanol, THF or dioxane and the resulting mixture is stirred for about 5 minutes to about 2 hours. After cooling the reaction mixture to a temperature from about 15° C. to about −10° C., mineral acid, preferably HCl, is added to destroy excess sodium borohydride and the alcohol is removed, preferably under reduced pressure, to yield the compound of formula 6.

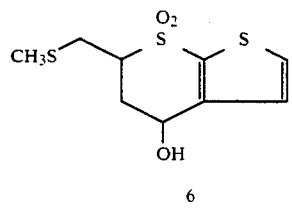

A tertiary amine, for example, a trialkylamine, preferably triethylamine, is added to a stirred solution of the compound of formula 6 and methanesulfonic anhydride in a polar solvent such as, for example, THF. After about one hour at about ambient temperature, the volatiles are removed, preferably under reduced pressure, to yield the compound of formula 7.

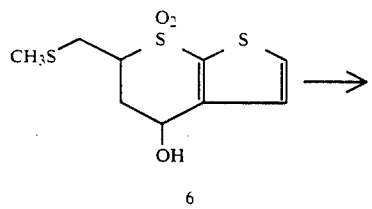

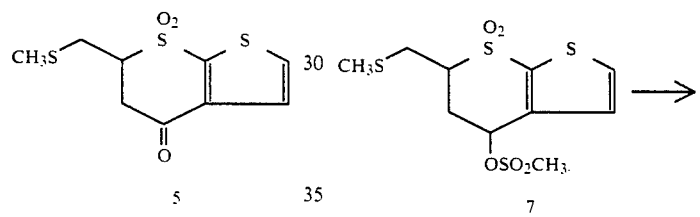

A mixture of sodium azide and the compound of formula 7 in dimethylsulfoxide (DMSO) is stirred at about ambient temperature for about 10 to about 30 hours to yield the product of formula 8.

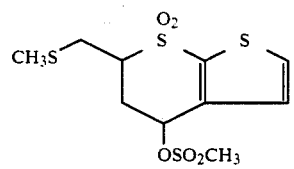

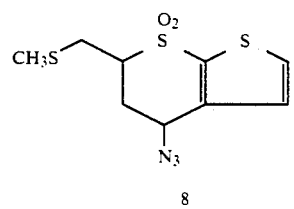

A mixture of the compound of formula 8 and triphenylphosphine in a polar solvent, for example, THF, is stirred at about ambient temperature for about 20 minutes to about 5 hours. An aldehyde of formula $R_1CHO$ wherein $R_1$ has the same meaning as defined previously, is added and stirring is continued for about 10 hours to about 30 hours. The resulting solution is added to a suspension of sodium borohydride in an alcohol, preferably ethanol, at a lowered temperature from about 15° C. to about −15° C. and stirred for about 10 minutes to about 3 hours. Excess sodium borohydride is destroyed by the addition of mineral acid, for example, HCl to give the compound of formula 9. To prepare compounds of formula 9 wherein $R_7$ is other than H, to the generated amine from the previous step is added a tertiary amine such as triethylamine or pyridine followed by a compound of formula $$\underset{R_7}{\overset{R_1CHX}{|}}$$

wherein $R_1$ and $R_7$ have the meaning defined previously and X is halide followed by stirring for about 10 hours to about 30 hours. The reaction mixture is then poured into a basic solution such as $NaHCO_3$ and aqueous hydroxide followed by extraction with an organic solvent such as diethyl ether, ethyl acetate, methylene chloride or chloroform.

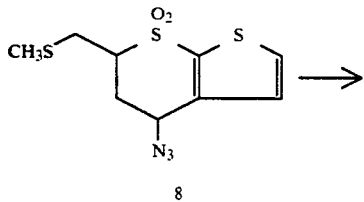

8

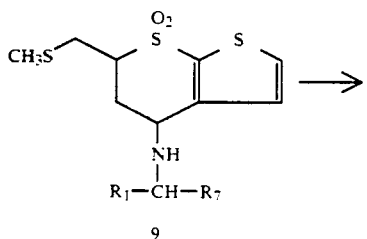

9

A solution of the compound of formula 9 is aqueous alkali such as, for example, NaOH, KOH, LiOH or $NH_4OH$, and THF is heated to reflux for about 0.5 hour to about 5 hours to give the compound of formula 10.

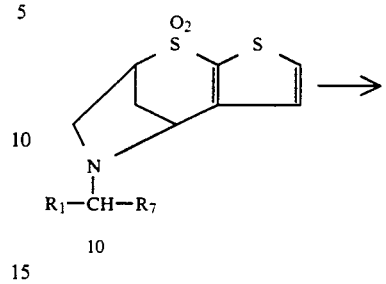

10

A solution of lithium bis(trialkylsilyl)amide, preferably, lithium bis(trimethylsilyl)amide, in a nonpolar solvent such as, for example, hexane, or in a polar solvent such as, for example, THF, is added to a stirred solution of the compound of formula 10 and a compound of formula $R_4X$ wherein X is a halide, preferably bromine, and $R_4$ has the meaning defined previously, in a polar solvent such as, for example, THF at lowered temperatures, typically at from about 0° C. to about −100° C., preferably at about −78° C., to give the compound of formula 11. Specific examples of compounds of the formula $R_4X$ are methyl bromide, methoxypropyl bromide, methylthioethyl bromide, 2-(2-methoxyethoxy)ethyl bromide or 2-(2-methylthioethylthio)ethyl bromide. When $R_4$ contains a sulfur atom, the corresponding sulfoxide or sulfone analogues can be prepared by standard oxidative procedures such as, for instance, those described for the preparation of the compounds of formulas 17 and 19.

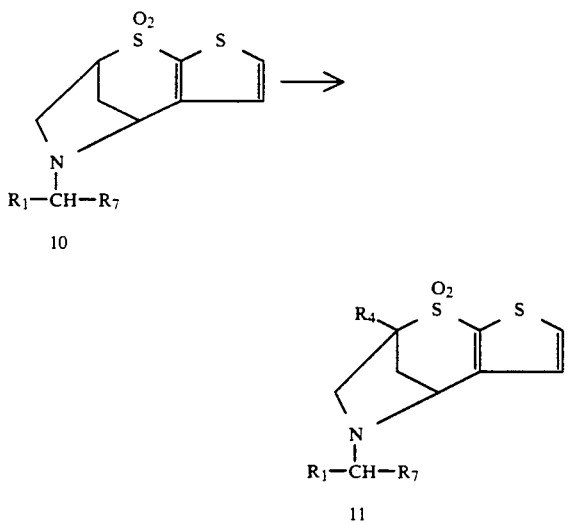

A solution of alkyl lithium, preferably butyl lithium, in a nonpolar solvent such as, for example, hexane is added to a solution of the compound of formula 11 in a polar solvent such as, for example, THF, at lowered temperatures, typically from about −50° C. to about −100° C., preferably at about −78° C. After from about 10 minutes to about 2 hours at this temperature, $SO_2$ is introduced over the surface of the cold stirred mixture for from about 1 minute to about 10 minutes. The solvent is removed under reduced pressure and the residue is dissolved in an alkali metal solution, preferably sodium acetate hydrate, and hydroxylamine-O-sulfonic acid is added, and the resulting reaction mixture is stirred for about 3 hours to about 15 hours at about ambient temperature. The mixture is then adjusted to about pH 7.5 by addition of alkali, preferably $NH_4OH$, to give the compound of formula 12.

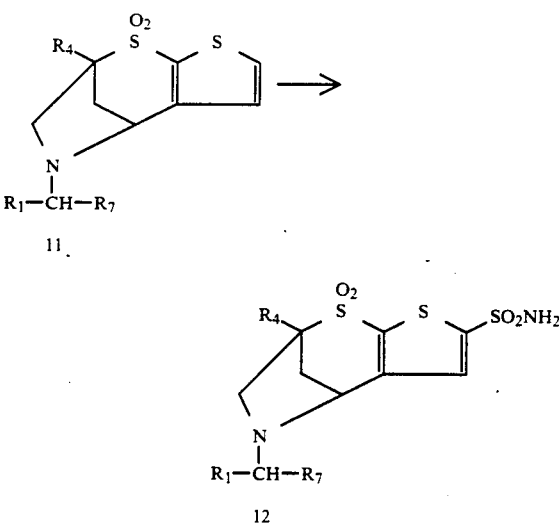

Alternatively, compounds of formula 14 can be prepared by heating at from about 50° C. to about 100° C. in the presence of base, such as LiOH, KOH, NaOH or NH$_4$OH in H$_2$O, compounds of formula 13, where X is CH$_3$S—, CH$_3$O—, CH$_3$OCH$_2$CH$_2$O—, $^+$N(CH$_3$)$_3$, or any other leaving group.

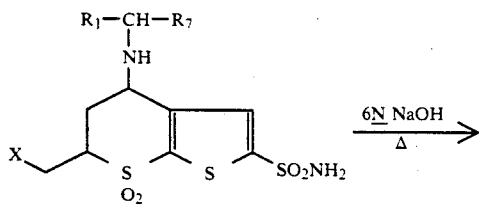

$\xrightarrow{\text{6N NaOH}, \Delta}$

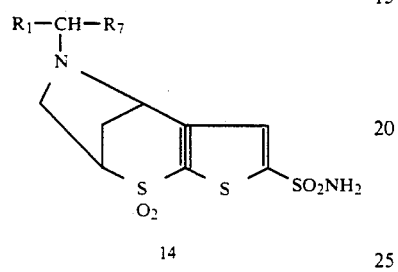

14

Another route to compounds described in this invention involves cyclization of compounds of formula 15 wherein n is 0, 1 or 2 with trialkyl aluminum, preferably trimethyl aluminum in an inert solvent such as toluene, benzene, THF, CHCl$_3$ or CH$_2$Cl$_2$ to yield the cyclic lactam of formula 16.

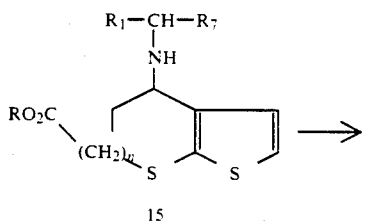

15

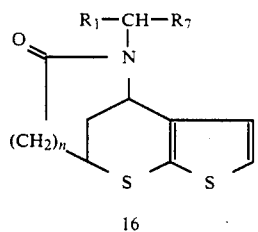

16

The lactam 16 can be oxidized using normal oxidizing agents such as Oxone ®, H$_2$O$_2$, m-chloroperbenzoic acid in aqueous alcohol and the like to yield the 1,1-dioxide derivative followed by reduction of the lactam with borane-dimethysulfide in an inert solvent such as, for example, THF, Et$_2$O, CH$_2$Cl$_2$ and the like, to yield the cyclic amine 17. Alternatively, controlled oxidation of lactam 16 with, for instance, NaIO$_4$, followed by redction of the lactam moiety yields the corresponding sulfoxide derivative 19.

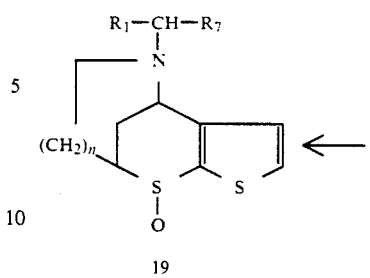

19

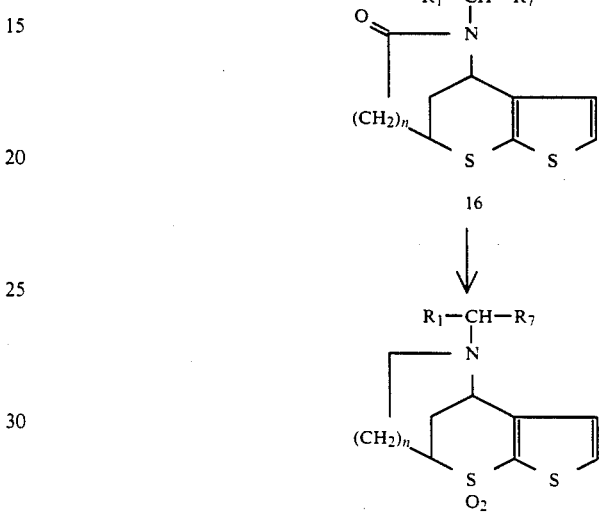

16

↓

17

Compounds of formula 18 can be obtained by alkylation of 17 using lithium bis(trialkylsilyl)amides such as lithium bis(trimethylsilyl)amide in an inert solvent such as hexane at temperatures of from about −100° C. to about −50° C. Alkyl halides such as methyl iodide, ethyl iodide, benzyl chloride or sulfonates such as methoxyethoxytrifluoromethane sulfonate and the like can be used as alkylating agents. Subsequently, incorporation of the 2-sulfonamido group is accomplished using methods previously described such as alkyllithium followed by treatment with SO$_2$ and hydroxylamine-O-sulfonic acid to yield the compound of formula 18. To generate compounds wherein R$_1$=H, the p-methoxybenzyl protecting groups can be removed in a known fashion using ceric ammonium nitrate or a variety of other reagents. Using essentially the same procedure but substituting either the compound of formula 16 or the compound of formula 19 for that of 17 the corresponding sulfonamides of formulas 20 and 21 are obtained.

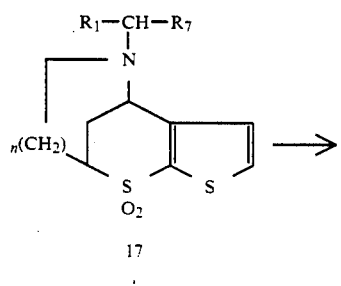

17

-continued

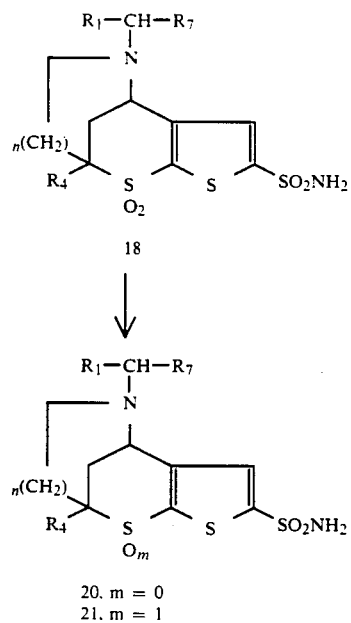

20. m = 0
21. m = 1

The novel pharmaceutical formulations of this invention can be adapted for oral administration such as tablets, capsules or the like; for nasal administration, especially in the form of a spray; for injection, in the form of a sterile injectable liquid; or for topical ocular administration in the form of solutions, suspensions, ointments, solid water soluble polymeric inserts, or gels.

This invention is particularly concerned with formulations adapted for topical ocular administration for the treatment of glaucoma and other stages of elevated intraocular pressure and contain from about 0.1% to about 15% by weight of medicament, especially from about 0.5 to about 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately pharmacologically equal amounts.

The novel method of treatment of this invention comprises the treatment of elevated intraocular pressure by the administration of a novel compound of this invention or a pharmaceutical formulation thereof. Of primary concern is the treatment by topical ocular administration of from about 0.1 to about 25 mg and especially from about 0.2 to about 10 mg of such compound per day, either by single dose or on a 2 to 4 dose per day regimen.

The following examples illustrate the present invention without, however, limiting the same thereto.

EXAMPLE 1

Preparation of 4-Ethyl-2-[2-(2-methoxyethoxy)ethyl]-2,3,4,5-tetrahydro-2,5-methanothieno[3,2-f]-1,4-thiazepine-7-sulfonamide-1,1-dioxide hydrochloride Step A: 6-Dimethylaminomethyl-5,6-dihydro-7,7-dioxo-4H-thieno[2,3-b]-thiopyran-4-one, ethylene ketal

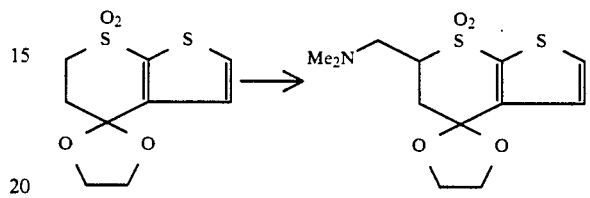

To a stirred solution of 5,6-dihydro-7,7-dioxo-4H-thieno[2,3-b]thiopyran-4-one, ethylene ketal (12 g, 49 mmol) in dry THF (250 ml), under nitrogen at −78° C., was added a solution of lithium bis(trimethylsilyl)amide in hexane (100 ml, 1M, 100 mmol) over 5-10 minutes. After 0.5 hour at −78° C., N,N-dimethylmethyleneammonium iodide (10 g, 54 mmol) was added and the reaction mixture was allowed to warm to 10° C. The reaction mixture was diluted with 10% ammonium chloride solution (500 ml) and extracted with ethyl acetate (3×300 ml). The combined organic extracts were washed with water (2×100 ml), brine (2×150 ml) and dried ($Na_2SO_4$). Removal of the filtered, dried solvent gave 10 g of crude solid. Trituration with 1-chlorobutane provided 7.5 g of solid material, used directly in the next step.

Step B: 6-Methylene-5,6-dihydro-7,7-dioxo-4H-thieno[2,3-b]thiopyran-4-one, ethylene ketal

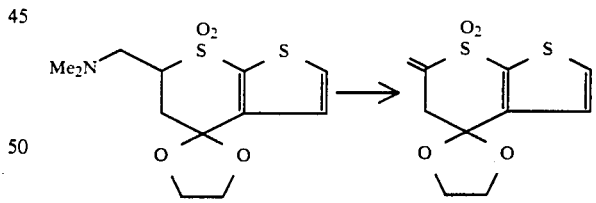

A mixture of the product from Step A (15 g, 49 mmol) and methyl iodide (30 ml) in THF (250 ml) was stirred at ambient temperature for twenty-four hours. The reaction mixture was diluted with ether and filtered. The filtered solid was dissolved in acetonitrile (200 ml) and treated with 1,8-diazabicyclo[5.4.0]undec-7-ene (7.5 g, 49 mmol). After stirring for approximately two hours, the solvent was removed under reduced pressure and the residue was partitioned between water and ethyl acetate. The ethyl acetate layer was washed with brine and dried ($Na_2SO_4$). Removal of the filtered, dried solvent under reduced pressure gave 9.2 g of solid, used directly in the next step.

Step C:
5,6-Dihydro-7,7-dioxo-6-methyl(thiomethyl)-4H-thieno[2,3-b]-thiopyran-4-one, ethylene ketal

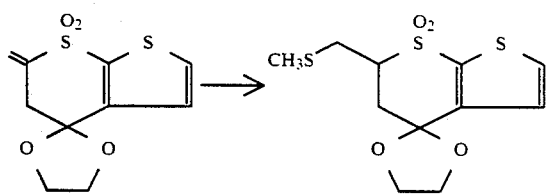

Sodium methanethiolate (2.5 g) was added to a stirred mixture of the product from Step B (9.15 g, 35 mmol) and THF (200 ml). After 0.5 hour, the solvent was removed in vacuo and the residue was partitioned between water and ethyl acetate. The organic layer was washed with water, brine and dried (MgSO$_4$). Removal of the filtered, dried solvent gave 9.5 g of yellowish solid, used directly in the next step.

Step D:
5,6-Dihydro-7,7-dioxo-6-methyl(thiomethyl)4H-thieno[2,3-b]-thiopyran-4-one

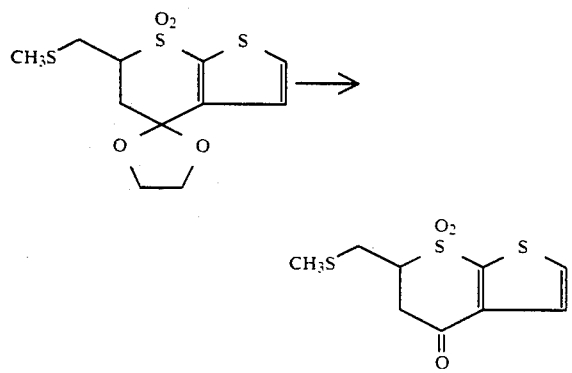

A solution of the product from Step C (9.5 g, 31 mmol) in 6N hydrochloric acid (200 ml) and THF (200 ml) was heated to reflux for about 0.5 hour. The THF was removed under reduced pressure, the residue was filtered and the solid was washed with water until the washings were neutral. The damp solid was used directly in the next step.

Step E: 5,6-Dihydro
4-hydroxy-6-methyl(thiomethyl)4H-thieno[2,3-b]thiopyran-7,7-dioxide

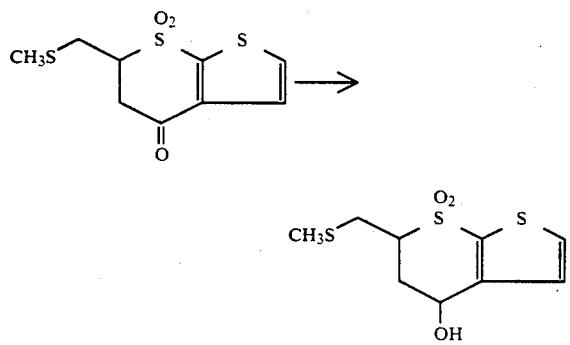

Sodium borohydride (0.60 g, 15.5 mmol) was added to a solution of the product from Step D (8.5 g, 31 mmol) in ethanol (150 ml) and the resulting mixture was stirred for 0.5 hour. After cooling the reaction mixture to 0°–5° C., excess sodium borohydride was destroyed by the addition of 6N hydrochloric acid. The ethanol was removed under reduced pressure, the residue treated with water (150 ml) and extracted with ethyl acetate (3×200 ml). The combined extracts were washed with brine and dried (MgSO$_4$). Evaporation of the filtered, dried solvent gave 7.8 g of an oil, used directly in the next step.

Step F:
5,6-Dihydro-4-methanesulfonyloxy-6-methyl(thiomethyl)-4H-thieno[2,3-b]thiopyran-7,7dioxide

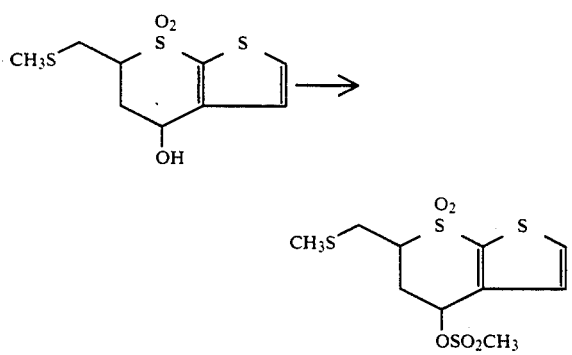

Triethylamine (11.5 ml, 83 mmol) was added to a stirred solution of the product from Step E (7.3 g, 28 mmol) and methanesulfonic anhydride (5.76 g, 33 mmol) in THF (400 ml). After one hour at ambient temperature, the volatiles were removed under reduced pressure. The residue was partitioned between water and ethyl acetate. The ethyl acetate layer was washed with water, brine and dried (MgSO$_4$). Evaporation of the filtered, dried solvent gave 10 g of an oil, used directly in the next step.

Step G:
4-Azido-5,6-dihydro-6-methyl(thiomethyl)-4H-thieno[2,3-b]thiopyran-7,7-dioxide

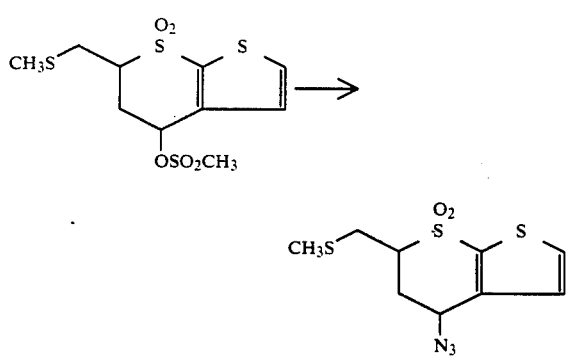

A mixture of sodium azide (2.5 g, 38 mmol) and the product from Step F (10 g, 32 mmol) in DMSO (100 ml) was stirred at ambient temperature for twenty-four hours. The reaction mixture was diluted with water and extracted with ethyl acetate. The organic layer was washed with water, brine and dried (MgSO$_4$). Removal of the filtered, dried solvent under reduced pressure gave 7.8 g of crude solid. Trituration with 1-chlorobutane provided 5.8 g of dried solid used directly in the next step.

Step H:
5,6-Dihydro-4-ethylamino-6-methyl(thiomethyl)-4H-thieno[2,3-b]thiopyran-7,7-dioxide

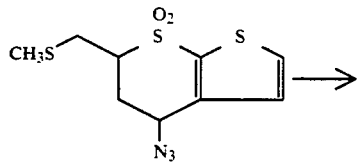

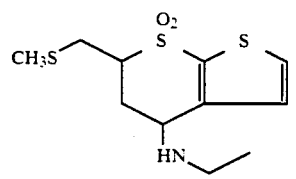

A mixture of triphenylphosphine (2.45 g, 9.4 mmol) and the product from Step G (2.38 g, 7.8 mmol) in THF (25 ml) was stirred at ambient temperature for two hours. Acetaldehyde (7 ml) was added to the reaction mixture and stirring was continued for twenty-four hours. The resulting solution was added to a suspension of sodium borohydride (2.96 g, 78 mmol) in ethanol (300 ml) at 0° C., stirred for 0.5 hour and excess sodium borohydride destroyed by the addition of 6N hydrochloric acid. The residue from removal of the volatiles under reduced pressure was partitioned between water and ethyl acetate. The acidic aqueous phase was neutralized with ammonium hydroxide and extracted with ethyl acetate. The extracts from the neutralized aqueous phase were washed with brine and dried (Na$_2$SO$_4$). Removal of the filtered, dried solvent gave 2.7 g of crude product. Ether extraction and evaporation gave 2.1 g of material used directly in the next step.

Step I:
4-Ethyl-2,3,4,5-tetrahydro-2,5-methanothieno[3,2-f]-1,4-thiazepine-1,1-dioxide

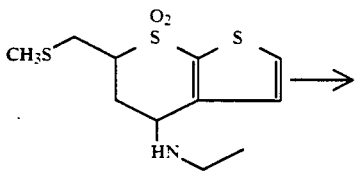

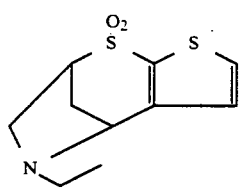

A solution of the product from Step H (3 g, 10 mmol) in 5% aqueous sodium hydroxide (100 ml) and THF (200 ml) was heated to reflux for two hours. The cooled reaction mixture was diluted with brine (100 ml) and extracted with ethyl acetate. The organic extracts were washed with brine and dried (Na$_2$SO$_4$). Removal of the filtered, dried solvent under reduced pressure gave 2.47 g of an oil that slowly solidifed. This material was used directly in the next step.

Step J:
4-Ethyl-2-[2-(2-methoxyethoxy)ethyl]-2,3,4,5-tetrahydro-2,5-methanothieno[3,2-f]-1,4-thiazepine-1,1-dioxide

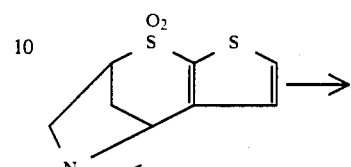

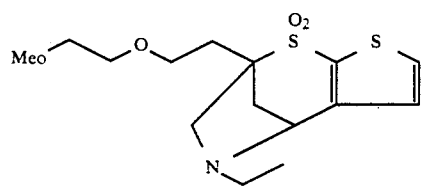

A solution of lithium bis(trimethysilyl)amide in hexane (12.8 ml, 1M, 12.8 mmol) was added to stirred solution of the product from Step I (2.4 g, 9.9 mmol) and 2-(2-methoxyethoxy)ethyl bromide (2.67 ml, 3.6 g, 20 mmol) in THF (50 ml) at −78° C. The reaction mixture was allowed to warm to ambient temperature, diluted with brine and extracted with ethyl acetate. The organic layer was washed with brine and dried (Na$_2$SO$_4$). Removal of the filtered, dried solvent gave 1.4 g of an oil which was used directly in the next step.

Step K:
4-Ethyl-2-[2-(2-methoxyethoxy)ethyl]-2,3,4,5-tetrahydro-2,5-methanothieno[3,2-f]-1,4-thiazepine-7,7-sulfonamide-1,1-dioxidehydrochloride

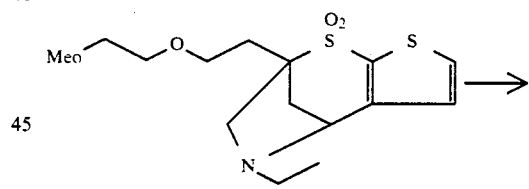

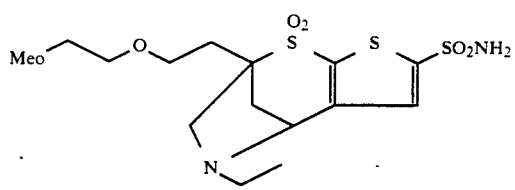

A solution of butyl lithium in hexane (2.7 ml, 2.5M, 6.7 mmol) was added to a solution of the product from Step J (1.15 g, 3.3 mmol) in THF (20 ml) at −78° C. After 0.5 hour at this temperature, sulfur dioxide was introduced over the surface of the cold stirred mixture for two minutes. The solvent was removed under reduced pressure, and the residue was dissolved in a solution of sodium acetate hydrate (0.97 g, 10 mmol) in water (20 ml). Hydroxylamine-O-sulfonic acid (1.12 g, 10 mmol) was added and the resulting reaction mixture was stirred for seven hours at ambient temperature. The mixture was adjusted to pH 7.5 by the addition of ammonium hydroxide. After ethyl acetate extraction of the crude product and chromatographic purification (silica gel, CHCl₃:CH₃OH, 95:5), there was obtained 0.60 g of off-white solid. The material was converted to the hydrochloride salt with ethanolic hydrogen chloride. Trituration of this solid with ether and ethyl acetate gave material of mp 93° C. (foams).

Anal. Calc'd for C₁₅H₂₄N₂O₆S₃+HCl (461.04): C, 39.08; H, 5.47; N, 6.08. Found: C, 39.18; H, 5.71; N, 5.80.

EXAMPLE 2

Preparation of 5-(4-Methoxybenzyl)-2-methyl-3,4,5,6-tetrahydro-2H-2,6-methanothieno[3,2-g]-1,5-thiazocine-8-sulfonamide-1,1-dioxide

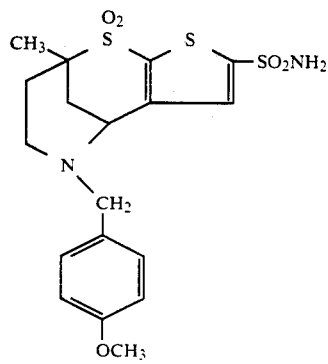

Step A: Preparation of cis Ethyl 5,6-Dihydro-4-(4-methoxybenzylamino)-4H-thieno[2,3-b]thiopyran-2-ylacetate

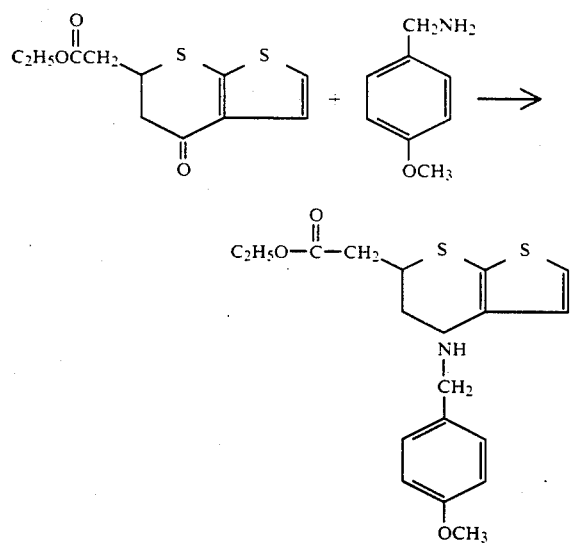

To a solution of ethyl 5,6-dihydro-4-oxo-4H-thieno[2,3-b]-thiopyran-6-ylacetate (10 g, 39 mmol) in THF (110 ml) and toluene (110 ml) at 0° C. was added 4-methoxybenzylamine (25.5 ml, 26.8 g, 195 mmol). Titanium tetrachloride (2.2 ml, 3.8 g, 20 mmol) was added to the cold solution and the resulting mixture was stirred for 0.75–1 hour. The mixture was added to a cold (0° C.) stirred suspension of sodium borohydride (4.5 g, 120 mmol) in EtOH (900 ml). The resulting mixture was stirred for about 1 hour and acidified to pH1 with 3N hydrochloric acid. The solvent was removed in vacuo and the residue partitioned between ethyl acetate and sodium bicarbonate solution. The ethyl acetate layer was separated, dried over anhydrous sodium sulfate and evaporated to give a mixture of cis and trans isomers of the title compound. Flash chromatography on silica gel eluting with ethyl acetate/hexane (1:4) gave 9.7 g of cis isomer after solvent removal and drying.

Step B: Preparation of 5-(4-Methoxybenzyl)-4-oxo-3,4,5,6-tetrahydro-2H-2,6-methano[3,2-g]-1,5-thiazocine

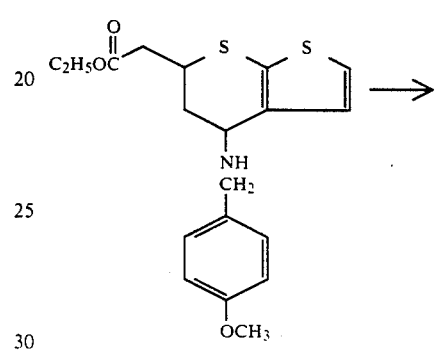

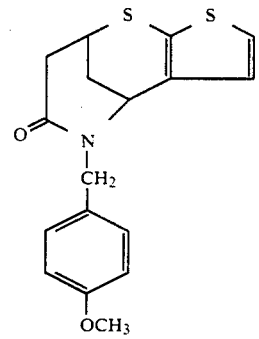

A solution of (CH₃)₃Al in toluene (23 ml, 2M, 46 mmol) was added to a stirred solution of the product from Step A (8.7 g, 23 mmol) in toluene (575 ml) at 0° C. The reaction mixture was brought to ambient temperature and then heated to reflux for four hours. The reaction mixture was cooled in an ice bath and treated with 3N hydrochloric acid (100 ml) and diluted with H₂O (500 ml) and ethyl acetate (500 ml). The layers were separated and the organic phase was washed with H₂O, brine and dried over anhydrous sodium sulfate. Removal of the filtered, dried solvent under reduced pressure gave 6.6 g of crude product. Recrystallization from hexane/ethylacetate gave material of mp 123°–125° C.

Anal. Calc'd for C₁₇H₁₇NO₂S₂ (331.47): C, 61.60; H, 5.18; N, 4.23. Found: C, 61.75; H, 5.15; N, 4.42.

Step C: Preparation of 5-(4-Methoxybenzyl)-4-oxo-3,4,5,6-tetrahydro-2H-2,6-methano[3,2-g]-1,5-thiazocine-1,1-dioxide

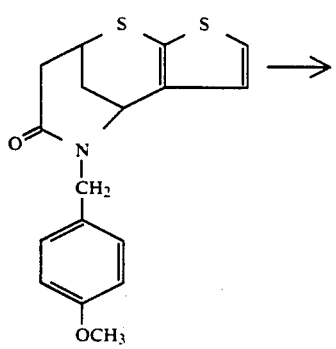

A solution of Oxone® (0.83 g, 1.35 mmol) in H₂O (12.4 ml) was added to a stirred solution of the product from Step B (0.15 g, 45 mmol) in CH₃OH (6.2 ml). After stirring for two hours, the reaction mixture was extracted with ethyl acetate. The organic layer was washed with 10% aqueous sodium bisulfite solution, brine and dried over anhydrous sodium sulfate. Removal of the filtered, dried solvent gave 0.14 g of crude product. Two recrystallizations from hexane/ethyl acetate provided material of mp 196°–198° C.

Anal. Calc'd for $C_{17}H_{17}NO_4S_2$ (363.47): C, 56.17; H, 4.72; N, 3.85. Found: C, 56.24; H, 4.68; N, 3.85.

Step D: Preparation of 5-(4-Methoxybenzyl)-3,4,5,6-tetrahydro-2-H-2,6-methano[3,2-g]-1,5-thiazocine-1,1-dioxide

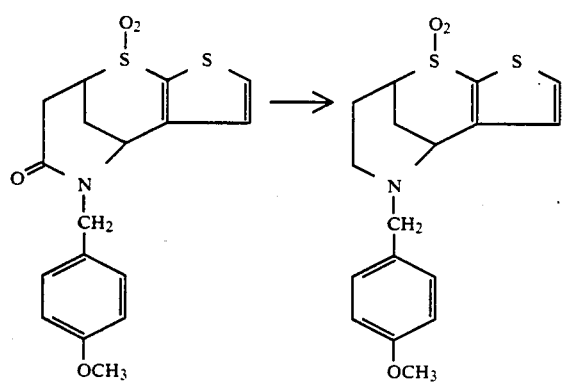

A solution of the product from Step C (1.0 g, 2.8 mmol) and borane dimethylsulfide (0.84 ml, 10M in THF, 8.4 mmol) in THF (11 ml) was heated under reflux for two hours. The solvent was removed and the residue was heated with 6N hydrochloric acid (8.5 ml) for 20 minutes to destroy the amine borane complex. The cooled mixture was neutralized with aqueous sodium bicarbonate solution and extracted with ethyl acetate. The organic extract was dried over anhydrous sodium sulfate, filtered and evaporated under reduced pressure to give an off-white foam. Flash chromatography over silica gel eluting with 40% ethyl acetate/60% hexane provided material of mp 167°–168° C.

Anal. Calc'd for $C_{17}H_{19}NO_3S_2$ (349.49): C, 58.42; H, 5.49; N, 4.01. Found: C, 58.42; H, 5.53; N, 4.04.

Step E: Preparation of 5-(4-Methoxybenzyl)-2-methyl-3,4,5,6-tetrahydro-2H-2,6-methanothieno[3,2-g]-1,5-thiazocine-1,1-dioxide

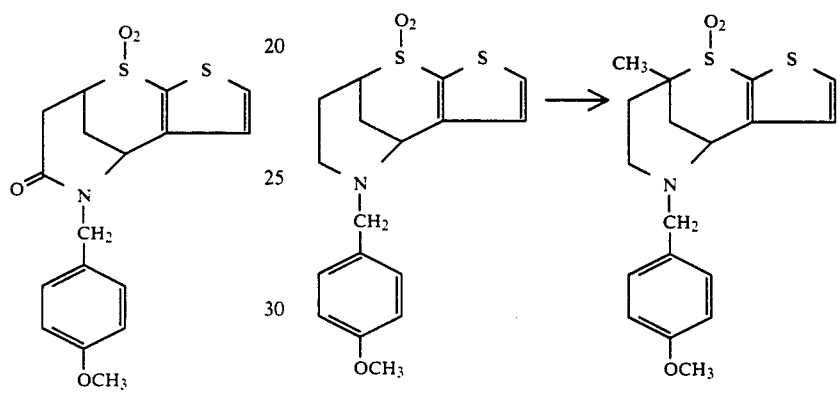

A solution of lithium bis(trimethylsilyl)amide in hexanes (28 ml, 1M, 28 mmol) was added dropwise to a stirred solution of the product from Step D (8.0 g, 23 mmol) in THF (200 ml) at −78° C. When addition was complete, methyl iodide (6.5 g, 46 mmol) was added at this temperature, then the reaction mixture was allowed to warm to ambient temperature and stirred overnight. The solvent was removed under reduced pressure and the residue was taken up in H₂O (300 ml) and extracted with ethyl acetate (3×300 ml). The combined organic extracts were washed with brine and dried over anhydrous sodium sulfate. Removal of the filtered, dried solvent under reduced pressure, followed by flash chromatography (silica gel, 30% ethyl acetate/70% hexane) of the residue (8.4 g) gave 6.5 g of white solid, used directly in the next step.

¹H-nmr: (CDCl₃) δ1.81(3H, S, 2—CH₃); 3.81 (3H, S, —OCH₃).

Step F: Preparation of 5-(4-Methoxybenzyl)-2-methyl-3,4,5,6-tetrahydro-2H-2,6-methanothieno[3,2-g]-1,5-thiazocine-8-sulfonamide-1,1-dioxide

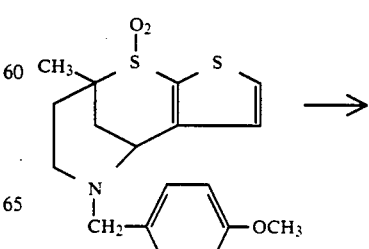

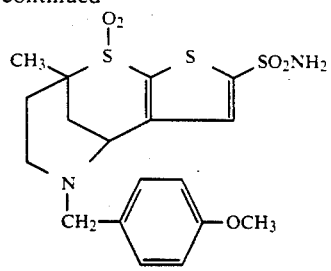

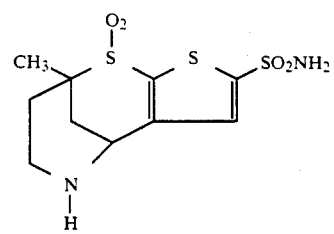

A solution of butyl lithium in hexane (8.0 ml, 2.5M, 20 mmol) was added to a stirred solution of the product from Step E (6.3 g, 17 mmol) in THF (145 ml) at −78° C. After stirring at this temperature for two hours, sulfur dioxide was introduced over the surface of the stirred reaction mixture for twenty minutes. The reaction mixture was stirred an additional 0.25 hour at this temperature and allowed to warm to ambient temperature. The solvent was removed under reduced pressure and the residue was dissolved in a solution of sodium acetate trihydrate (6.5 g, 48 mmol) in water (62 ml) at 0° C. Hydroxylamine-0-sulfonic acid (4.6 g, 41 mmol) was added and the mixture was stirred overnight at ambient temperature. The mixture was treated with a solution of saturated sodium bicarbonate solution (50 ml), diluted with water (1500 ml) and extracted with ethyl acetate. The organic extracts were washed with brine and dried over anhydrous sodium sulfate. Removal of the filtered, dried solvent under reduced pressure followed by trituration of the residue with ethyl acetate and methanol gave 4.0 g of white solid. An additional 1.4 g was obtained from flash chromatography (silica gel, 40% ethyl acetate, 60% hexane) of the material obtained by evaporation of the trituration solvents. Recrystallization from methanol-ethyl acetate-hexane gave material of mp 254°–256° C.

Anal. Calc'd for $C_{18}H_{22}N_2O_5S_3$ (442.60): C, 48.84; H, 5.02; N, 6.33. Found: C, 48.85; H, 5.06; N, 6.06.

EXAMPLE 3

Preparation of 5-(4-Methoxybenxyl)-2-methoxypropyl-3,4,5,6-tetrahydro-2H-2,6-methanothieno[3,2-g]-1,5-thiazocine-8-sulfonamide-1,1-dioxide The title compound, mp 190°–193° C., was prepared following the procedure of steps A–F of Example 2, but substituting methoxypropyl iodide for methyl iodide in Step E.

EXAMPLE 4

Preparation of 2-Methyl-3,4,5,6-tetrahydro-2H-2,6-methanothieno[3,2-g]-1,5-thiazocine-8-sulfonamide-1,1-dioxide hydrochloride

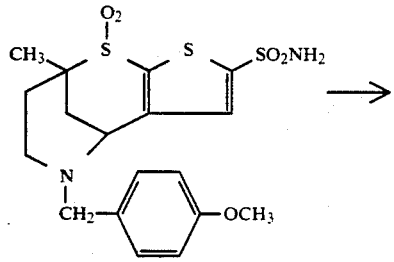

A solution of ceric ammonium nitrate (32.9 g, 60 mmol) in water (76 ml) was added to a solution of 5-(4-methoxybenzyl)-2-methyl-3,4,5,6-tetrahydro-2H-2,6-methanothieno[3,2-g]-1,5-thiazocine-8-sulfonamide-1,1-dioxide (5.2 g, 12 mmol) in acetonitrile (790 ml). After stirring for 24 hours at ambient temperature, the acetonitrile was removed under reduced pressure. The resulting mixture was diluted with water, made alkaline by the addition of aqueous ammonia and extracted with ethyl acetate. The ethyl acetate layer was washed with brine and dried over anhydrous sodium sulfate. The residue obtained from evaporation of the filtered, dried solvent was chromatographed (silica gel, $CHCL_3/MeOH/NH_4OH$, 90:10:1) to give 1.9 g of off-white solid. Treatment with methanolic hydrogen chloride, followed by recrystallization from methanol gave material of mp >290° C.

Anal. Calc'd for $C_{10}H_{14}N_2O_4S_3+HCl$ (358.90): C, 33.46; H, 4.22; N, 7.81. Found: C, 33.31; H, 3.87; N, 7.57.

EXAMPLE 5

Preparation of 2-Methoxypropyl-3,4,5,6-tetrahydro-2H-2,6-methanothieno[3,2-g]-1,5-thiazocine The title compound, mp 265°–267° C., was prepared following the procedure of steps A, B, D and E of Example 2, but substituting methoxypropyl iodide for methyl iodide in Step E, and then following the procedure of Example 4.

EXAMPLE 6

5-Isobutyl-4-oxo-3,4,5,6-tetrahydro-2H-2,6-methanothieno[3,2-g]-1,5-thiazocine-8-sulfonamide

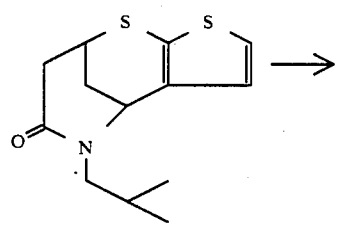

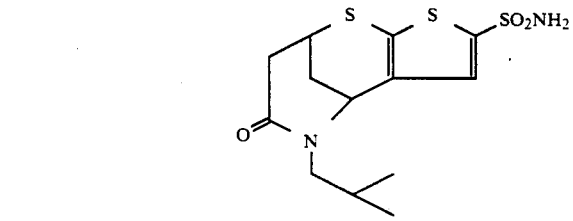

5-Isobutyl-4-oxo-3,4,5,6-tetrahydro-2H-2,6-methanothieno[3,2-g]-1,5-thiazocine, prepared as described in Example 2, steps A and B but substituting isobutylamine for 4-methoxybenzylamine (4 g, 15 mmol), was added to a mixture of phosphorous pentachloride (6.23 g, 30 mmol) and chlorosulfonic acid (7 ml) at 0° C. After 0.5 hour at this temperature and 0.5 hour at 50° C., the reaction mixture was poured over crushed ice. The resulting sulfonyl chloride was separated and treated with concentrated aqueous ammonia (100 ml) in ethyl acetate (100 ml) at 0° C. The ethyl acetate layer was separated and evaporated under reduced pressure. The resulting solid was chromatographed over silica gel (ethyl acetate: hexane; 1:1) to give 2.0 g of the title compound.

EXAMPLE 7

5-Isobutyl-4-oxo-3,4,5,6-tetrahydro-2H-2,6-methanothieno[3,2-g]-1,5-thiazocine-8-sulfonamide-1,1-dioxide

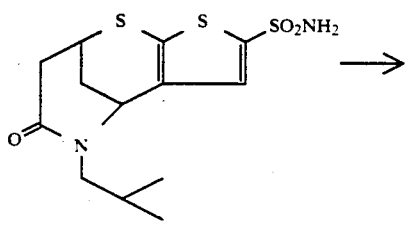

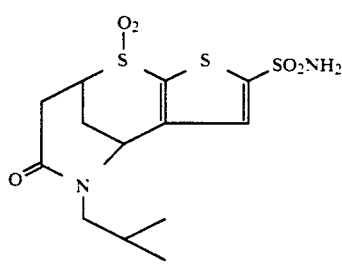

5-Isobutyl-4-oxo-3,4,5,6-tetrahydro-2H-2,6-methanothieno[3,2-g]-1,5-thiazocine-8-sulfonamide (2 g, 5.8 mmol) was added to a mixture of Oxone® (10 g, 16.3 mmol) and methanol (25 ml). After 24 hours, the reaction mixture was diluted with water (50 ml) and extracted with ethyl acetate (3×50 ml). After drying over sodium sulfate, the solvent was evaporated under reduced pressure to yield 2.13 of a foam. A sample triturated with 1-chlorobutane gave material with mp 239°–241° C.

Anal. Calc'd for $C_{13}H_{18}N_2O_5S_3$ (378.50): C, 41.25; H, 4.80; N, 7.40. Found: C, 41.48; H, 4.78; N, 7.24.

EXAMPLE 8

5-Isobutyl-3,4,5,6-tetrahydro-2H-2,6-methanothieno[3,2-g]-1,5-thiazocine-8-sulfonamide-1,1-dioxidehydrochloride

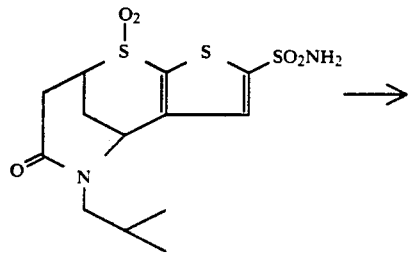

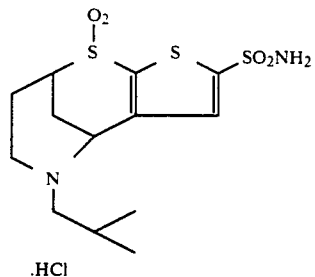

A solution of borane dimethyl sulfide in THF (5.5 ml, 10M, 55 mmol) was added to a solution of 5-isobutyl-4-oxo-3,4,5,6-tetrahydro-2H-2,6-methanothieno[3,2-g]-1,5-thiazocine-8-sulfonamide-1,1-dioxide (2.1 g, 5.5 mmol) in THF (25 ml) and heated at reflux for two hours. Dilute hydrochloric acid (25 ml, 3N) was added and refluxing was continued for an additional two hours. The THF was removed under reduced pressure, the residue was diluted with water (50 ml), saturated sodium bicarbonate solution (50 ml) and extracted with ethyl acetate (3×50 ml). The ethyl acetate extracts were washed with brine, dried ($Na_2SO_4$) and evaporated to give 1 g of off-white solid. The material was converted to the hydrochloride salt with ethanolic hydrogen chloride, mp 264°–265° C.

Anal. Calc'd for $C_{13}H_{20}N_2O_4S_3$+HCl (401.02): C, 38.93; H, 5.29; N, 6.99. Found: C, 38.99; H, 5.29; N, 6.89.

EXAMPLE 9

5-Propyl-3,4,5,6-tetrahydro-2H-2,6-methanothieno[3,2-g]-1,5-thiazocine-8-sulfonamide-1,1-dioxide hydrochloride The title compound, mp 282°–283° C. (dec), was prepared following the procedures of example 6–8 except using as starting material in example 6 5-propyl-4-oxo-3,4,5,6-tetrahydro-2H-2,6-methanothieno-[3,2-g]-1,5-thiazocine, which was prepared as described in Steps A and B of Example 2 substituting propylamine for 4-methoxybenzylamine.

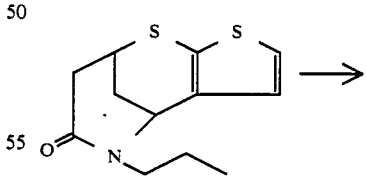

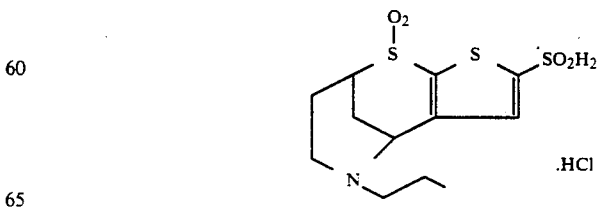

Anal. Calc'd for $C_{12}H_{18}N_2O_4S_3$+HCl (386.94): C, 37.24; H, 4.68; N, 7.23. Found: C, 36.92; H, 4.80; N, 7.20.

EXAMPLE 10

2,5-Methanothieno[3,2-f]-1,4-thiazepine-7-sulfonamide-4-propyl-2,3,4,5-tetrahydro-1,1-dioxide.HCl

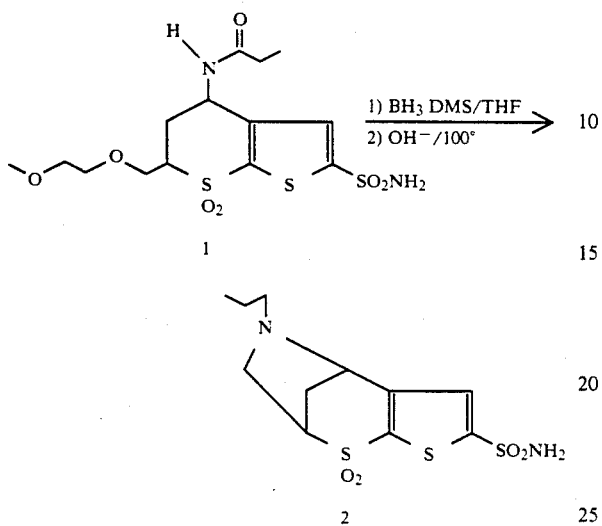

Using a short path distillation head attached to a 3-N flask, amide 1 (15.8 g, 0.037 m) and THF (160 ml) were added. To the stirred suspension under $N_2$, 10M borane.dimethylsulfide (17 ml, 0.17 mol) was added carefully. After addition, the reaction was heated to 60° C. and dimethylsulfide (bp 40° C.) was collected in the distillation apparatus along with THF. After heating at 60° C. for 2 hours, the reaction mixture was concentrated to dryness and then 6N NaOH (160 ml) was added carefully to the residue and the solution heated at reflux. After 1.5 hours the solution was stirred at room temperature overnight. The solution was neutralized to pH 7 with 6N HCl and extracted with EtOAc (3×). The organic extracts were dried, filtered and concentrated to dryness. The residue was chromatographed on a Still column (100 mm) and the product eluted with $CHCl_3:CH_3OH$ (20:1) to yield 5.4 g of product. The material was crystallized as the HCl salt from EtOH-HCl to yield 4.1 g (30%) of 2; mp 281°-2° C.

Anal. Calc'd for $C_{11}H_{16}N_2O_4S_3.HCl$: C, 35.43; H, 4.60; N, 7.51. Found: C, 35.51; H, 4.48; N, 7.42.

EXAMPLE 11

Cis(S,S)2,5-methanothieno[3,2-f]-1,4-thiazepine-7-sulfonamide-4-ethyl-2,3,4,5-tetrahydro-1,1-dioxide.HCl

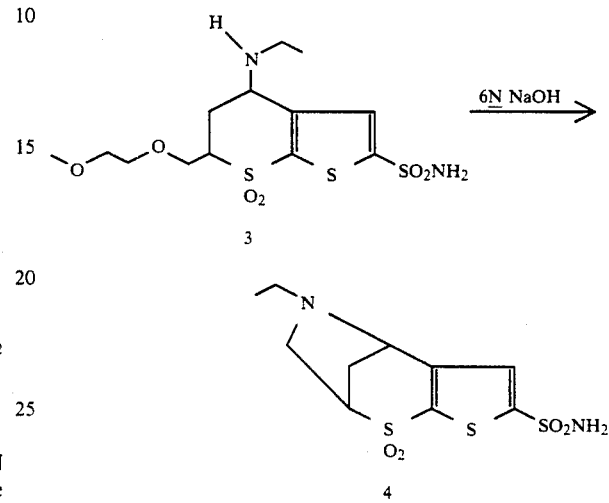

Under $N_2$, 3, trans (S,R) (0.22 g, 0.51 mmol) and 6N NaOH (5 ml) were heated at reflux. After 1.5 hours, the solution was adjusted to pH 8.5 with 6N HCl and saturated $NaHCO_3$ and the aqueous layer was extracted with EtOAc (3×). The organic layers were dried, filtered and concentrated to dryness. The residue was treated with EtOH-HCl, concentrated to dryness and crystallized from EtOH to yield 0.116 g (71%) of 4; m.p. 200°-202°; $\alpha_D^{25} = -21.5°$ (C=0.805, $CH_3OH$).

Anal. Calc'd for $C_{10}H_{14}N_2O_4S_3.HCl.H_2O$: C, 31.86; H, 4.55; N, 7.43. Found: C, 32.00; H, 4.26; N, 7.25.

EXAMPLE 12

Following the chemistry described above as well as, where needed, standard organic chemistry techniques, the following compounds also can be prepared.

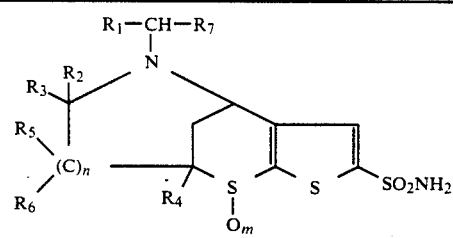

| $R_1$ | $R_7$ | $R_2$ | $R_3$ | n | $R_5$ | $R_6$ | $R_4$ | m |
|---|---|---|---|---|---|---|---|---|
| $-CH_2CH_3$ | H | H | H | 0 | — | — | H | 1 |
| $-CH_2CH(CH_3)_2$ | H | H | H | 1 | H | H | $CH_3SCH_2CH_2-$ | 2 |
| $-CH_2CH_2CH_3$ | H | H | H | 1 | H | H | $CH_3SCH_2CH_2SCH_2CH_2-$ | 2 |
| $-CH_2CH_3$ | H | H | H | 1 | H | H | $CH_3OCH_2CH_2SO2CH_2CH_2-$ | 2 |
| $-CH_2CH_2CH_2CH_3$ | H | $CH_3$ | H | 0 | — | — | H | 2 |
| $-CH_2CH_3$ | H | H | H | 1 | $CH_3$ | — | H | 2 |
| $-CH_2CH(CH_3)_2$ | H | H | H | 1 | $CH_3CH_2$ | — | H | 2 |
| $-CH_2CH_2CH_3$ | H | H | H | 0 | — | H | H | 0 |
| $-CH_2CH_2CH_3$ | H | H | H | 1 | H | H | $CH_3CH_2NHCH_2CH_2-$ | 2 |
| $-CH_2CH(CH_3)_2$ | H | H | H | 1 | H | H | $CH_3OCH_2CH_2NHCH_2CH_2-$ | 2 |
| $-CH_2CH_3$ | $CH_3$ | H | H | 0 | — | — | H | 0 |
| $-CH_2CH_3$ | H | $CH_3$ | $CH_3$ | 1 | H | H | H | 2 |

-continued

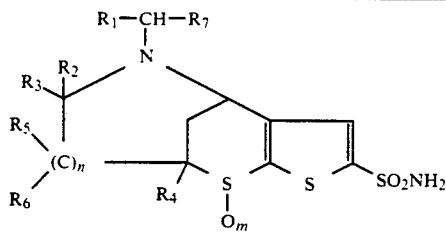

| R₁ | R₇ | R₂ | R₃ | n | R₅ | R₆ | R₄ | m |
|---|---|---|---|---|---|---|---|---|
| —CH=CH₂ | H | H | H | 1 | H | H | H | 2 |
| —CH₂CH₂OCH₃ | H | H | H | 1 | H | H | H | 2 |
| —CH₂CH₂CH₂OH | H | H | H | 1 | H | H | H | 2 |
| —CH₂CH₃ | H | H | H | 0 | — | — | HOCH₂CH₂— | 2 |
| —CH₂CH₂CH₃ | H | H | H | 1 | H | H | HOCH₂CH₂OCH₂— | 2 |
| —CH₂CH₂CH₃ | H | H | H | 1 | H | H | CH=CHCH₂OCH₂— | 2 |
| —CH₂CH₂SCH₃ | H | H | H | 1 | H | H | HOCH₂CH₂SOCH₂CH₂— | 2 |
| —CH₂CH₂CH₂F | H | H | H | 1 | H | H | CH₃OCH₂CH₂CH₂— | 2 |
| —CH₂(CH₂)₂CH₃ | H | H | H | 1 | CH₃ | CH₃ | CH₃CH₂CH₂— | 2 |
| —CH₃ | H | H | H | 1 | H | H | CH₃CH₂CH₂— | 2 |
| —CH₃ | H | H | H | 0 | — | — | CH₃CH₂CH₂— | 2 |
| —CH₃ | H | H | H | 2 | H | H | CH₃CH₂CH₂— | 2 |
| —CH₂CH₃ | H | H | H | 2 | H | H | CH₃— | 2 |
| —CH₂CH₃ | H | H | H | 2 | H | H | CH₃CH₂— | 2 |
| —CH₂CH₃ | H | H | H | 2 | H | H | CH₂=CHCH₂OCH₂— | 2 |
| —CH₂CH₃ | H | H | H | 2 | H | H | CH₃OCH₂CH₂OCH₂CH₂CH₂— | 2 |
| —CH₃ | H | H | H | 2 | H | H | CH₃CH₂OCH₂CH₂O(CH₂)₃— | 2 |
| —CH₃ | H | H | H | 2 | H | H | CH₃O(CH₂)₃O(CH₂)₃— | 2 |

What is claimed is:

1. A compound of the formula:

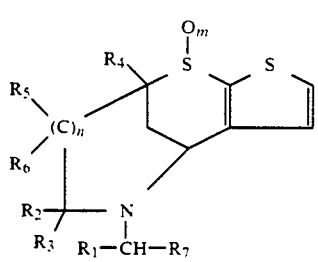

wherein $R_1$ is H, unsubstituted or substituted lower alkyl, lower alkenyl, aryl or aralkyl wherein the aryl groups optionally are substituted; $R_2$, $R_3$, $R_5$, $R_6$ and $R_7$ are independently H or alkyl or $R_2$ and $R_3$ together can be =O, $R_4$ is H, lower alkyl, lower alkenyl or lower alkyl substituted by hydroxy, alkoxy, hydroxyalkoxy, lower alkenyloxy, alkoxyalkoxy, hydroxyalkoxyalkoxy, alkylamino, hydroxyalkylamino, alkoxyalkylamino, hydroxyalkoxyalkylamino, alkyl-S(O)$_m$-, hydroxyalkyl-S(O)$_m$-, alkoxyalkyl-S(O)$_m$-, hydroxyalkoxyalkyl-S(O)$_m$-, alkyl-S(O)$_m$-alkoxy, hydroxyalkylS(O)$_m$-alkoxy, alkyl-S(O)$_m$alkyl-S(O)$_m$ and hydroxyalkyl-S(O)$_m$alkyl-S(O)$_m$; and m and n are independently 0, 1, or 2.

2. A compound of the formula:

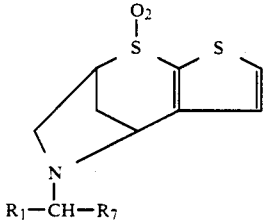

wherein $R_1$ and $R_7$ are as defined in claim 1.

3. A compound of the formula:

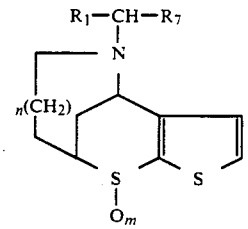

wherein $R_1$, $R_7$, m and n are as defined in claim 1.

* * * * *